United States Patent [19]

Buehler et al.

[11] 4,054,658

[45] Oct. 18, 1977

[54] THERAPEUTIC COMPOSITIONS CONTAINING METHAQUALONE

[75] Inventors: John D. Buehler, 02, Fort Washington; Pramod B. Chemburkar, Willow Grove; Robert S. Joslin, Fort Washington, all of Pa.

[73] Assignee: William H. Rorer, Inc., Fort Washington, Pa.

[21] Appl. No.: 651,132

[22] Filed: Jan. 21, 1976

Related U.S. Application Data

[63] Continuation of Ser. No. 440,053, Feb. 6, 1974, abandoned, which is a continuation of Ser. No. 43,976, June 5, 1970, abandoned.

[51] Int. Cl.² ......................................... A61K 31/505
[52] U.S. Cl. ................................................... 424/251
[58] Field of Search ........................................ 424/251

[56] References Cited

U.S. PATENT DOCUMENTS

| 3,162,634 | 12/1964 | Klosa | 424/251 |
| 3,406,173 | 10/1968 | Heusner et al. | 424/251 |
| 3,515,787 | 6/1970 | Breuer et al. | 424/251 |

OTHER PUBLICATIONS

Chemical Abstracts, vol. 55 (1961), p. 3933f.
Chemical Abstracts, vol. 63 (1965), p. 1120d.
Schwartz et al, "Surface Active Agents," vol. I (1949), p. 457.

*Primary Examiner*—V. D. Turner
*Attorney, Agent, or Firm*—Erich M. H. Radde

[57] ABSTRACT

A therapeutic composition of methaqualone and the like quinazolinone compounds or their acid addition salts per se or in combination with other therapeutic agents, said composition containing solubilizing adjuncts and being rapidly and readily absorbed, and methods of making and using same.

9 Claims, No Drawings

THERAPEUTIC COMPOSITIONS CONTAINING METHAQUALONE

This is a continuation, of application Ser. No. 440,053 filed Feb. 6, 1974, now abandoned, which in turn is a continuation of Ser. No. 43,976 filed on June 5, 1970, now abandoned.

BACKGROUND OF THE INVENTION

1. FIELD OF THE INVENTION

This invention relates to a therapeutic composition and to methods of preparing compositions containing the sedative hypnotic drug methaqualone or the like compounds and their acid addition salts as well as to a method for the manufacture of methaqualone or the like compounds in solid dosage preparations to enhance the rate of solution and absorption of methaqualone or the like compounds, thereby producing a more rapid and-/or greater degree of sedation or hypnosis for a given weight of said sedative agents.

2. DESCRIPTION OF THE PRIOR ART

Methaqualone, i.e., 2-methyl-3-(o-tolyl)-4(3H)-quinazolinone is a known, orally effective compound with valuable hypnotic, anticonvulsant, and sedative properties which is used in therapy as central nervous system calmative agent and central muscle relaxant. Boissier et al. describe in "Therapie" vol. 22, pp. 129-135 (1967) a number of 2-methyl-3-phenyl-4(3H)-quinazolinone compounds which are substituted in the phenyl ring by other substituents than methyl and which also possess hypnotic, anticonvulsant and sedative properties. Especially valuable compounds of this group are 2-methyl-3-(2-chloro phenyl)-4(3H)-quinazolinone known as mecloqualone, 2-methyl-3-(2,4-dichlorophenyl)-4(3H)-quinazolinone, 2-methyl-(2-chloro-4-methylphenyl)-4(3H)-quinazolinone, 2-methyl-3-(4-chlorophenyl)-4(3H)-quinazolinone, and other compounds of the formula

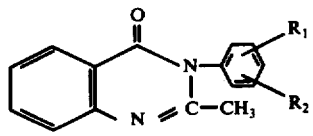

wherein
$R_1$ is chloro or lower alkyl such as methyl or ethyl, and
$R_2$ is hydrogen, chloro, or methyl.

To be effective after oral administration, a sedative or hypnotic agent such as methaqualone or the like compounds in a solid dosage form such as a tablet or capsule must be available for absorption from the gastrointestinal tract. For a sedative or hypnotic agent to act promptly, such absorption should occur very soon after ingestion of the drug. The first step in absorption is the dissolution of the active components in the gastric juice. Furthermore, rapid dissolution of the active compound would result not only in a more rapid absorption and pharmacologic response, but also in more complete absorption of the drug from the gastrointestinal tract, i.e., a high percentage of the drug will be absorbed and will exert its intended action if it dissolves rapidly and completely.

The heretofore available solid dosage forms of methaqualone and the like compounds, however, have the disadvantage that their rate of dissolution and absorption from the gastro-intestinal tract is rather low and that, therefore, less satisfactory sedative or hypnotic effects are achieved.

SUMMARY OF THE INVENTION

It is one object of the present invention to provide a valuable pharmaceutical composition in solid dosage form comprising methaqualone and the like compounds or their pharmaceutically acceptable acid addition salts, said composition being more rapidly dissolved by the gastric juices, thereby producing a more rapid onset and/or a greater degree of sedation of hypnosis for a given weight of methaqualone or the like compound and thus exerting a more pronounced and prolonged sedative or hypnotic effect than the heretofore available methaqualone or the like preparations.

Another object of the present invention is to provide a simple and effective process of preparing such a valuable methaqualone or the like composition.

A further object of the present invention is to provide a method of causing sedation or hypnosis in humans by administering such methaqualone or the like composition, thereby producing a more rapid onset and/or a greater degree of sedation or hypnosis for a given weight of methaqualone or the like compound than heretofore possible.

Other objects of the present invention and advantageous features thereof will become apparent as the description proceeds.

In principle the composition according to the present invention is characterized by having incorporated therein an agent or agents which are capable of increasing the rate of dissolution and, as a result thereof, the rate of absorption of the methaqualone or the like compounds from the gastro-intestinal tract. A composition in dosage unit form according to the present invention contains for sedative or hypnotic purposes between about 25 mg. and about 300 mg. and preferably between about 150 mg. and about 250 mg. of methaqualone or the like compounds which are administered in tablet, pill, dragee, capsule, or the like solid dosage forms. Included into said composition are adjuncts to aid in increasing the rate of dissolution of the methaqualone or the like compounds. These adjuncts may be present in a range of from about 0.5% to about 3500%, by weight, of the methaqualone or the like compounds content depending upon the specific adjuncts used and the rapidity, duration, and degree of sedation or hypnosis desired.

The solubilizing adjuncts disclosed in this invention comprise
 a. a surfactant (0.5% to 300%, by weight), and/or
 b. an acidifier (10% to 1000%, by weight), and/or
 c. an aggregation preventing carrier, i.e. a carrier providing a large surface of methaqualone or the like compounds (100% to 2000%, by weight), and-/or
 d. a dispersant (0.5% to 50%, by weight),
the indicated percentages being the percent of adjunct in relation to the content of the methaqualone or the like compounds or their salts in the dosage form. In producing such a therapeutic composition according to the present invention, the surfactant, the acidifier, carrier, and the dispersant may be present with and in combination with the methaqualone or the like particles in any suitable combination and the inclusion of any one or more of these adjuncts would fall within the scope of this invention and would serve to some degree to promote a more rapid dissolution of the methaqualone or the like compound when ingested and utilized as described herein. At least one of these agents capable of increasing the rate of dissolution must be present in an effective amount in the composition. Preferred compositions are those which contain at least two of said solubilizing adjuncts.

The surfactants may be selected from any one of several types of surfactants, any of which promote the wetting and dissolution of methaqualone or the like particles. Examples of such surfactants are, for instance, the following:

The polyoxypropylene-polyoxyethylene nonionics described by Kirk-Othmer in "Encyclopedia of Chemical Technology" 2nd edition, vol. 19, page 553-554 (1969) and especially those which are marketed by Wyandotte Chemical Corp. under their PLURONIC trademark;

the polyoxyethylene glycol esters of higher fatty acids described by Kirk-Othmer, l.c. pages 541-545 (1969) and especially those marketed by Geigy Chemical Corp., Inc. under their NONISOL trademark; by Atlas Chemical Industries, Inc. under their MYRJ trademark; and by Glyco Chemicals, Inc. under their ALDOSPERSE trademark;

the alkyl phenoxy poly(ethyleneoxy) ethanols or ethoxylated alkyl phenols described by Kirk-Othmer, l. c., pages 533-536 (1969) and especially those marketed by Rohm and Haas Co. under their TRITON trademark;

the ethoxylated aliphatic alcohols or alkyl poly(ethyleneoxy) ethanols described by Kirk-Othmer, l. c. pages 536-539 (1969) and especially those marketed by Atlas Chemical Industries, Inc. under their BRIJ trakemark;

the organic phosphoric acid esters of complex structure described by Kirk-Othmer, l.c., pages 529-531 (1969) and especially those marketed by GAF Corporation under their GAFAC trademark;

the polyoxyethylene derivatives of sorbitan fatty acid esters described by Kirk-Othmer, l. c., pages 545-548 (1969) and especially those marketed by Atlas Chemical Industries, Inc. under their TWEEN trademark;

lecithin;

and others.

These have all been found to be beneficial toward the end of wetting and dissolving of the primary component methaqualone and the like compounds.

The acidifier or acidic salt may be taken preferably from any number of amino acids and their salts such as glycine hydrochloride, lysine hydrochloride, glutamic acid hydrochloride, and the like which are capable of reducing the pH of the gastric fluid in the environment immediately surrounding the methaqualone and the like particles and thus will promote dissolution of the powder. Other suitable organic or inorganic acids or acidic salts may also be used.

The absorption enhancing and aggregation preventing carrier material according to the present invention preferably comprises any organic or inorganic material or combination thereof which serves to assist in dispersing the methaqualone and the like particles, prevent aggregation of said particles in the composition, and allows rapid contact of the methaqualone and the like compounds with the solubilizing fluid. Useful carriers are, for instance, starch, mannitol, sorbitol, lactose, sucrose, polyethylene glycol of a molecular weight between about 1,000 and about 6,000, and preferably of a molecular weight of 4,000, microcrystalline cellulose such as sold by American Viscose Division of FMC Corporation under the trademark AVICEL, the carbohydrate preparation sold under the trademark CELUTAB by Penick & Ford and being composed of 92% dextrose and 8% higher saccharides, and others.

The dispersant can be a finely divided silica or silicate such as the microfine precipitated silica marketed by Philadelphia Quartz Co. under their QUSO trademark; by the Davison Chemical Division of W. R. Grace & Co. under their SILOID trademark which is vapor phase hydrolyzed silica gel; by Cabot Corporation under their CAB-O-SIL Trademark which is submicroscopic fumed silica; and others. Such dispersants, when employed as described hereinafter, will assist in preventing aggregation of the drug particles in the dosage form.

A highly critical feature and an inherent part of the present invention with respect to achieving rapid dissolution and absorption of methaqualone or the like compounds is the process of manufacture by which methaqualone or the like compounds or their acid addition salts are combined with the acidifier and/or surfactants and especially with the carrier and/or the dispersant, to produce a pharmaceutical dosage form. The process of producing the pharmaceutical dosage form of methaqualone or the like compounds according to the present invention is specifically designed to provide discrete particles of said drugs of large surface area without aggregation occurring. As a result of the specific procedure in making the composition rapid dissolution and hence rapid in vivo absorption is achieved. It is an essential characteristic of the process according to the present invention that at least the majority of the methaqualone or the like particles are separated and remain separate from each other in the composition according to this invention.

The following procedures have proved to produce the readily absorbable methaqualone or the like compositions according to the present invention:

a. Deposition of the particles of the drug from their solution on the solubilizing adjuncts, preferably on the carrier.

b. Micronizing of the drug or its salts without aggregation together with the adjuncts and especially with the carrier and/or the dispersant.

c. Spray drying of solutions or suspensions of the drug or its salts together with one or more of the adjuncts, d. Dissolving of the drug or its salts in the molten adjuncts such as a meltable surfactant, and causing solidification of the molten mixture under conditions whereby the drug will crystallize in a fine state of subdivision.

Deposition of methaqualone or the like compound per se or in combination with a soluble adjunct, for instance, a soluble surfactant upon a carrier is effected by dissolving said compound with or without a surfactant and/or an acidifier in a suitable solvent, for instance, in methylene chloride, methanol, isopropanol, chloroform, carbon tetrachloride, cyclohexane, hexane, heptane, and others, and intimately mixing the solution with the carrier and, if desired, the dispersant in such a way that uniform distribution of the compound throughout the carrier occurs. The solvent is subsequently removed by drying. If desired, the other adjuncts, such as the acidifier, surfactant, and/or dispersant may be admixed and the resulting powder is processed by conventional pharmaceutical procedures to produce a solid dosage form, such as tablets or capsules which may be administered as a sedative or hypnotic with the benefits claimed herein.

Simple mixing and milling of methaqualone or the like compounds and the adjuncts, especially of the carrier and/or the dispersant does not produce the required solubility increasing and absorption improving effect because thereby aggregation of the particles of said compounds cannot be excluded. Milling with the carrier and/or the dispersant must be effected under conditions whereby methaqualone or the like compound is comminuted to a very fine degree of subdivision, for instance, to a particle size not substantially exceeding 20 $\mu$ and preferably smaller than about 5 $\mu$, whereby substantially no aggregation of such fine particles occurs, and whereby the particles of methaqualone or the like compounds or at least the majority thereof, are separated and remain separated from each other due to the presence of the carrier and/or dispersant particles which are interspersed between said particles. In order to achieve this result, milling is preferably effected in a high energy mill such as an air attrition mill through which the mixture of methaqualone or the like compound or their salt, acidifier, surfactant, carrier, and/or dispersant is passed until the average particle size of the components is preferably in the range of 1 $\mu$ to 5 $\mu$.

According to another process of improving absorption of methaqualone or the like compounds or their salts, said compound and the solubilizing adjuncts, if soluble, such as the surfactants, are dissolved in a suitable volatile solvent such as, for instance, methylene chloride or other suitable solvents as mentioned hereinabove. The solution is then spray dried preferably in a spray drier at an inlet temperature between about 65° C. and about 80° C. and an outlet temperature between about 30° C. and about 40° C. to produce a product in which the methaqualone is present in small discrete particles interspersed wit the adjunct and especially the surfactant. Of course, in this case an adjunct such as a surfactant must be selected which has suitable solvent solubility and solidification characteristics. Furthermore, the methaqualone or the like compound and the adjunct may be dissolved in a volatile solvent, to which is added a finely divided sparingly soluble or insoluble component the particles of which, upon spray drying, will serve as foci for the crystallization of methaqualone or the like compound and the deposition of the adjunct.

It is also possible to dissolve methaqualone or the like compounds or their salts in a suitable meltable adjunct such as a surfactant which was heated above its melting point. The melt containing the drug in the molten adjunct is then allowed to cool to room temperature and the resulting solid material is milled. In this case, it is not necessary to mill the resulting solidified mixture to a fine state of subdivision inasmuch as methaqualone or the like compound will have crystallized out with the adjunct as very fine particles. Preferably stirring of the molten mixture is continued while cooling until solidification starts to occur at which point the agitation is stopped. After milling, other adjuncts or therapeutic agents may be added, if desired, and a pharmaceutical dosage form is prepared using a suitable pharmaceutical procedure therefor.

Of course, other excipients, such as lubricants, binding agents, disintegrants, and others as they are known in pharmaceutical compounding may be added to the preparations prepared as described hereinabove containing the methaqualone or the like compound in very fine, non-aggregated particles.

The methaqualone, 2-methyl-3-(o-tolyl)-4(3H)-quinazoline and the like compounds such as referred to in the foregoing and all of the following descriptive paragraphs and examples may be present in the basic form or as one of their pharmaceutically acceptable acid addition salts such as the hydrochloride, sulfate, or nitrate. Furthermore, said compound may be present as the sole therapeutic ingredient of a pharmaceutical dosage form or it may be present in combination with other therapeutic components, such as diphenhydramine, methscopolamine, amphetamine, glutethimide, etodroxyzine, i.e., 8-[(4-chlorobenzhydryl)-1-piperazin-1-yl]-3,6-dioxaoctan-1-ol dimaleate, aminopyrine, meprobamate, chlorprothixen, bromodiethylacetyl carbamide, acetyl salicylic acid, codeine, or with one or more of the barbituric acid derivatives.

PREFERRED EMBODIMENTS OF THE INVENTION

The invention will be better understood from the following examples which are given for illustrative purposes only and are not meant to limit or restrict the invention.

EXAMPLE 1

150 g. of methaqualone and 150 g. of glycine hydrochloride are intimately mixed with each other. The resulting powder is filled into gelatin capsules, each containing 150 mg. of methaqualone.

EXAMPLE 2

250 g. of methaqualone and 250 g. of glutamic acid hydrochloride are intimately mixed with each other and are moistened with a solution of 25 g. of polyvinylpyrrolidone in 250 g. of isopropanol. The moistened mixture is granulated, whereby the solvent evaporates. Thereafter, 25 g. of starch powder and 5 g. of magnesium stearate are admixed to the granulated mass which is then compressed into tablets, each containing 250 mg. of methaqualone.

EXAMPLE 3

200 g. of methaqualone and 100 g. of lysine hydrochloride are intimately mixed with each other and with 15 g. of the silica dispersant known under the trademark CAB-O-SIL (manufacturer: Cabot Corporation) and 30 g. of magnesium stearate.

The resulting powder is filled into gelatin capsules, each containing 200 mg. of methaqualone.

The capsules and tablets containing the mixtures of methaqualone and acidifier of the above given examples are considerably more readily dissolved in the gastrointestinal fluids and thus more effective than capsules and tablets containing methaqualone alone.

EXAMPLE 4

250 g. of methaqualone and 500 g. of the polyoxypropylene-polyoxy-ethylene non-ionic surfactant known under the trademark PLURONIC F-68 (manufacturer: Wyandotte Chemical Corp.) are dissolved in 10 l. of methylene chloride. The solution is spray dried. The resulting spray dried mixture contains the methaqualone in particles of an average particle size not substantially exceeding 10 μ interdispersed with the surfactant. The resulting powder is densified, mixed with 4 g. of the silica dispersant known under the trademark QUSO (manufacturer: Philadelphia Quartz Co.), 12 g. of starch powder, and 4 g. of magnesium stearate and filled into capsules, each capsule containing 250 mg. of methaqualone.

EXAMPLE 5

250 g. of methaqualone, 125 g. of glycine hydrochloride as acidifier, 10 g. of microfine precipitated silica known under the trademark QUSO F-22 (manufacturer: Philadelphia Quartz Co.) as dispersant, and 5 g. of the surfactant known under the trademark PLURONIC F-98 are mixed and passed through an air attrition mill wherein the mixture is comminuted to an average particle size between 1 μ and 5 μ. The resulting powder is compressed into tablets using conventional pharmaceutical processes to produce a solid dosage form. Each tablet contains 250 mg. of methaqualone.

EXAMPLE 6

100 g. of methaqualone are dissolved in 300 g. of the molten polyoxyethylene monostearic acid ester surfactant known under the trademark MYRJ 45 (manufacturer: Atlas Chemical Industries).

The resulting solution is allowed to cool to room temperature in such a manner that the methaqualone crystallizes with the surfactant in the form of very fine particles. The resulting solid mixture is then milled with 150 g. of glycine hydrochloride as acidifier. The mixture is granulated with the addition of 55 g. of a starch paste, dried, and the granulated mixture is intimately mixed with 15 g. of starch powder and 6 g. of magnesium stearate. Tablets are compressed from the resulting mixture, each tablet containing 300 mg. of methaqualone.

EXAMPLE 7

200 g. of methaqualone and 25 g. of the polyoxyethylene monostearic acid ester surfactant known under the trademark ALDOSPERSE S-9 (manufacturer: Glyco Chemicals, Inc.) are dissolved in 600 cc. of methylene chloride. The solution is slowly dispersed in 500 g. of mannitol, 2.5 g. of the silica dispersant known under the trademark CAB-O-SIL, and 8 g. of magnesium stearate with concurrent removal of the methylene chloride so that the methaqualone and the surfactant are deposited on the mannitol substrate in such a way that uniform distribution of the methaqualone throughout the mannitol carrier is achieved.

50 g. of glycine hydrochloride are admixed thereto. The resulting powder is filled into gelatin capsules, each containing 200 mg. of methaqualone.

EXAMPLE 8

Composition:

250 g. of methaqualone, 500 g. of mannitol, 25 g. of the lauryl poly(ethyleneoxy) ethanol surfactant known under the trademark BRIJ 35 (manufacturer: Atlas Chemical Industries), 50 g. of glycine hydrochloride, and 0.5 g. of the microfine precipitated silica dispersant known under the trademark QUSO F-22 (manufacturer: Philadelphia Quartz Co.).

The procedure is the same as described in Example 7, whereby the dispersant is mixed with mannitol prior to the deposition thereon of the methaqualone and the surfactant from their solution in methylene chloride. The resulting powder is granulated by moistening it with a 5% gelatin solution. After drying, the granulated mixture is intimately mixed with 15 g. of starch and 5 g. of magnesium stearate and is compressed into tablets, each containing 250 mg. of methaqualone.

EXAMPLE 9

Composition:

100 g. of methaqualone, 5 g. of the tertiary octyl phenoxy poly(ethyleneoxy) ethanol surfactant known under the trademark TRITON X-114 (manufacturer: Rohm & Haas Co.), 500 cc. of methylene chloride, 500 g. of mannitol, 50 g. of glycine hydrochloride, and 25 g. of diphenhydramine hydrochloride.

The procedure is the same as described in Example 7, whereby methaqualone and the surfactant dissolved in methylene chloride are deposited on mannitol and the powder obtained after evaporation of the solvent is mixed with glycine hydrochloride and diphenhydramine hydrochloride. The resulting powder is compressed into tablets which are sugar coated to yield dragees, each containing 100 mg. of methaqualone and 25 mg. of diphenhydramine hydrochloride.

EXAMPLE 10

Composition:

250 g. of methaqualone, 125 g. of the surfactant PLURONIC F-68, 125 g. of glycine hydrochloride, and 25 g. of diphenhydramine hydrochloride.

The procedure is the same as described in Example 6, whereby methaqualone is dissolved in the surfactant and the heated mixture is allowed to cool to room temperature and then milled with the glycinehydrochloride and diphenhydramine hydrochloride. The milled mixture is filled into capsules with each capsule containing 250 mg. of methaqualone and 25 mg. of diphenhydramine hydrochloride.

EXAMPLE 11

Composition:

124 g. of methaqualone, 12 g. of the surfactant PLURONIC F-68, 6 g. of the dispersant QUSO F-22, and 60 g. of glycine hydrochloride.

The preparation of the composition proceeds in substantially the same manner as described in Example 5 whereby, however, the resultant powder is filled into capsules, each capsule containing 124 mg. of methaqualone.

EXAMPLES 12 TO 22

The procedure is the same as described hereinabove in Examples 1 to 11 whereby in place of methaqualone, the same amount of 2-methyl-3-(2-chlorophenyl)-4(3H)-quinazolinone, also known as mecloqualone, is used as active component.

In place of the bases methaqualone and mecloqualone, there can be used other 2-methyl-3-phenyl-4(3H)-quinazolinone compounds such as the 2-methyl-3-(2-ethylphenyl)-4(3H)-quinazolinone, or the pharmaceutically acceptable acid addition salts of such compounds such as their hydrochlorides.

Of course, other acidifiers, surfactants, carriers, and dispersants may be used than those mentioned in the preceding examples. The amounts of the adjuncts added may vary as stated hereinabove. Thus, the acidifiers in Examples 1 to 3 may amount to between 25 mg. and 1000 mg. and the surfactant in Example 7 may amount to between 2.5 mg. and 750 mg. per dosage unit form. The amounts of the adjuncts used in Examples 5 to 9 may also vary within the ranges given hereinabove. When proceeding according to Example 6, the amount of methaqualone should be selected so that it is substantially completely dissolved in the surfactant or other meltable adjunct.

PHARMACOLOGICAL TESTS

In order to prove that the serum methaqualone levels obtained with a composition according to the present invention wherein methaqualone has been converted into a readily absorbable form, are very considerably higher than when using methaqualone per se, dogs were administered identical amounts of methaqualone whereby Preparation A is a commercially available methaqualone powder, while Preparation B is a methaqualone composition prepared according to Example 10 by the solidified surfactant-methaqualone method.

These preparations were orally administered to dogs in amounts of 100 mg. of methaqualone/kg. of body weight. The serum methaqualone levels were determined from 30 minutes to 7 hours after administration.

The following Table I clearly shows that the serum methaqualone levels obtained with Formulation B were significantly higher than those obtained with Formulation A, which demonstrates the increased bio-availability of the drug from Formulation B according to the present invention.

TABLE I

| Formulation | Serum Methaqualone Level in μg./ml. Time after Administration | | | | | | | | | | | | |
|---|---|---|---|---|---|---|---|---|---|---|---|---|---|
| | 0 hour | | ½ hour | | 1 hour | | 2 hours | | 3 hours | | 5 hours | | 7 hours | |
| | A | B | A | B | A | B | A | B | A | B | A | B | A | B |
| Dog No. 9 | 0 | 0 | 0.8 | 2.9 | 1.5 | 4.1 | 2.6 | 5.7 | 2.8 | 7.6 | 1.2 | 4.4 | 0.7 | 2.6 |
| Dog No. 10 | 0 | 0 | 0.4 | 2.8 | 1.2 | 3.8 | 1.9 | 5.8 | 1.7 | 5.4 | 0.4 | 5.3 | 0.1 | 10.3 |
| Dog No. 11 | 0 | 0 | 0.4 | 0.5 | 1.4 | 1.5 | 1.6 | 3.3 | 1.6 | 5.8 | 0.6 | 8.2 | 0.1 | 4.2 |
| Dog No. 12 | 0 | 0 | 0.2 | 0.2 | 0.1 | 1.0 | 1.1 | 4.9 | 3.3 | 5.7 | 1.3 | 2.3 | 0.6 | 2.2 |
| Average | 0 | 0 | 0.5 | 1.6 | 1.0 | 2.6 | 1.8 | 4.9 | 2.4 | 6.1 | 0.9 | 5.0 | 0.4 | 4.8 |

Analogous tests were carried out with

Preparation C which is a methaqualone composition prepared according to Example 11 by the air attrition method, while Preparation D is a commercially available methaqualone powder.

Preparations C and D were also orally administered to dogs in the amounts of 100 mg. of methaqualone/kg. of dog body weight. The serum methaqualone levels were determined at the time periods and with the results indicated in the following Table II. The tests also demonstrate the increased bioavailability of methaqualone from Formulation C according to the present invention.

TABLE II

| Formulation | Serum Methaqualone Level in μg./ml. Time after Administration | | | | | | | | | | | | |
|---|---|---|---|---|---|---|---|---|---|---|---|---|---|
| | 0 hour | | ½ hour | | 1 hour | | 2 hours | | 3 hours | | 5 hours | | 7 hours | |
| | C | D | C | D | C | D | C | D | C | D | C | D | C | D |
| Dog No. 17 | 0 | 0 | 1.2 | 1.8 | 2.8 | 1.7 | 4.4 | 1.4 | 6.0 | 1.2 | 4.7 | 0.5 | 1.6 | 0.5 |
| Dog No. 18 | 0 | 0 | 2.0 | 1.4 | 2.6 | 1.3 | 3.9 | 0.4 | 2.4 | 0.4 | 1.0 | 0 | 0.9 | 0 |
| Dog No. 19 | 0 | 0 | 3.2 | 1.9 | 8.5 | 8.9 | 18.0 | 9.8 | 10.4 | 8.2 | 5.8 | 4.5 | 4.7 | 2.8 |
| Dog No. 20 | 0 | 0 | 0.7 | 0.1 | 3.5 | 0.6 | 4.7 | 0.8 | 7.8 | 0.8 | 4.5 | 0.8 | 3.2 | 0.8 |
| Average | 0 | 0 | 1.7 | 1.3 | 4.3 | 3.1 | 7.7 | 3.1 | 6.6 | 2.6 | 4.0 | 1.4 | 2.6 | 1.0 |

Preparations according to the present invention which contain other 2-methyl-3-phenyl-4(3H)-quinazolinone compounds showed also a considerably increased serum level when tested in the same manner. In general, the increase amounts to between about 200% and about 1200%. The prolonged effect of methaqualone and the like compounds in compositions according to the present invention which is due to their higher blood level, is especially noteworthy.

Oral administration to humans produced similar serum level increasing effects as observed in animal tests. The doses administered are about the same as administered heretofore, i.e., between about 50 mg. and about 300 mg. per dose.

We claim:

1. An orally administrable, rapidly soluble, and readily absorbable, sedative hypnotic composition comprising between 25 mg. to 300 mg. per dosage unit of 2-methyl-3-(o-tolyl)-4(3H)-quinazolinone and its pharmaceutically acceptable acid addition salts, and at least two adjuncts selected from the group consisting of:
   a surfactant effective for wetting and dissolving said quinazolinone present in an amount of 0.5% to 300% by weight of said quinazolinone and selected from the group consisting of a polyoxypropylene-polyoxyethylene nonionic compound, a polyoxyethylene glycol ester of a higher fatty acid, an alkyl phenoxy poly(ethyleneoxy)ethanol, an alkyl poly(ethyleneoxy)ethanol, a complex organic phosphoric acid, a complex organic phosphoric acid ester, a polyoxyethylene derivative of a sorbitan fatty acid ester, and lecithin;

an acidifier present in an amount between 10% and 1000% by weight of said quinazolinone and selected from the group consisting of hydrochlorides of glycine, glutamic acid and lysine;

an aggregation preventing carrier present in an amount between 100% and 2000% by weight of said quinazolinone and selected from the group consisting of mannitol, sorbitol, starch, lactose, sucrose, polyethylene glycol of a molecular weight between 1000 and 6000, and microcrystalline cellulose; and a dispersant present in an amount between 0.5% and 50% by weight of said quinazolinone and selected from the group consisting of finely divided silica and finely divided silicate;

said quinazolinone compound being present in said composition in the form of finely divided, discrete, substantially non-aggregated particles, wherein the particle size does not exceed 20μ, at least the majority of said particles being and remaining separate from each other, and the adjuncts being present in intimate contact with the discrete particles of said quinazolinone.

2. The composition of claim 1 in a tablet dosage form.

3. The composition of claim 1 in a capsule dosage form.

4. The composition of claim 1 wherein the quinazolinone is present in an amount of between about 150 mg. and about 250 mg.

5. The composition of claim 1 wherein the particle size of the quinazolinone is less than about 5μ.

6. The composition of claim 1 wherein the particle size of the components is in the range of 1μ to 5μ.

7. The composition of claim 1 wherein the acidifier is glycine hydrochloride and the dispersant is finely divided silica.

8. The composition of claim 1 which contains a polyoxypropylene-polyoxyethylene nonionic surfactant, a dispersant which is finely divided silica and an aggregation preventing carrier which is starch powder.

9. The composition of claim 1 which comprises a polyoxyethylene monostearic acid ester surfactant, glycine hydrochloride and starch.

* * * * *